(12) United States Patent
Noè et al.

(10) Patent No.: US 7,125,992 B2
(45) Date of Patent: Oct. 24, 2006

(54) PROCEDURE FOR THE PRODUCTION OF HIGH-PURITY MELAMINE WITH HIGH YIELDS

(75) Inventors: Sergio Noè, San Donato Milanese (IT); Massimo Parmegiani, Olgiate Olona (IT); Roberto Santucci, Gorla Maggiore (IT)

(73) Assignee: Eurotecnica Melamine Luxembourg Zweigniederlassung in Ittigen, Ittigen (CH)

( * ) Notice: Subject to any disclaimer, the term of this patent is extended or adjusted under 35 U.S.C. 154(b) by 58 days.

(21) Appl. No.: 10/479,931

(22) PCT Filed: May 30, 2002

(86) PCT No.: PCT/IT02/00348

§ 371 (c)(1),
(2), (4) Date: Feb. 23, 2004

(87) PCT Pub. No.: WO02/100839

PCT Pub. Date: Dec. 19, 2002

(65) Prior Publication Data

US 2004/0162429 A1     Aug. 19, 2004

(30) Foreign Application Priority Data

Jun. 8, 2001   (IT)   .............................. MI01A1216

(51) Int. Cl.
*C07D 251/62*   (2006.01)
*C07D 251/60*   (2006.01)

(52) U.S. Cl. ...................................... 544/201; 544/203
(58) Field of Classification Search ................ 544/201, 544/203

See application file for complete search history.

(56) References Cited

U.S. PATENT DOCUMENTS 3,637,686 A * 1/1972 Kokubu et al. ............. 544/203

FOREIGN PATENT DOCUMENTS

WO    WO 00/71525 A1    11/2000

* cited by examiner

*Primary Examiner*—Venkataraman Balasubramanian
(74) *Attorney, Agent, or Firm*—Serafini Associates; Franco A. Serafini

(57) ABSTRACT

A process for the production of high-purity melamine by pyrolysis of urea at high pressure, wherein the liquid phase output from the pyrolysis reactor is sent to a downstream post-reactor, and wherein the anhydrous gaseous phase from the pyrolysis reactor and from the post-reactor are subjected to washing with molten urea for the recovery of the melamine. The purified liquid exiting the post-reactor is treated in a quenching column, in order to eliminate poly-condensates, while the quenching column output is cooled. A high purity melamine is then separated by crystallization from a mother liquor, the greater part of which is recycled to the quenching column, thereby enabling a costless recovery of ammonia and melamine. The remaining mother liquor is treated for the separation of oxidized products of pyrolysis and is then sent back to the quenching column, thereby realizing the complete recovery of the melamine.

7 Claims, 2 Drawing Sheets

PROCEDURE FOR THE PRODUCTION OF HIGH-PURITY MELAMINE WITH HIGH YIELDS

BACKGROUND OF THE INVENTION

1. Field of the Invention

The present invention relates to an improved procedure for the production of high-purity melamine according to a process based on the pyrolysis of urea under high pressure.

In greater detail, the present invention refers to the process that provides for the collection and purification in aqueous solution of melamine produced in a reactor and its separation by crystallization.

2. Description of Related Art

The reaction transforming urea into melamine follows the stoichiometry shown in the following equation:

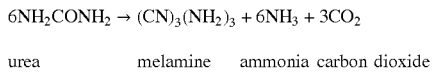

| urea | melamine | ammonia | carbon dioxide | according to which approximately 1.86 kilograms of a gaseous mixture of $NH_3$ and $CO_2$ (collectively called off-gas) are formed for every kilogram of melamine produced.

The most widely used process based on the pyrolysis of urea under high pressure is described in U.S. Pat. No. 3,161,638 to Allied. The basis of this process is that all effluents from the melamine synthesis reactor are cooled and collected in aqueous ammonia medium. The presence of ammonia as alkaline medium prevents the precipitation of the intermediate oxidation products of the pyrolysis reaction, called oxyaminotriazines (OAT) and enables the transformation into melamine of the de-ammoniating condensation by-products of the same (polycondensates), thus assuring a high degree of purity of the product.

According to this process, a stream of off-gas is also produced containing water vapor derived from the aforementioned treatment of the entire effluent of the reactor with an aqueous medium. This gaseous phase is normally returned to the urea synthesis plant in order to recover the $NH_3$ and the $CO_2$ contained in it. However, the presence of water vapor in the off-gas stream can constitute a problem for the urea plant.

Furthermore, the residual aqueous solution (mother liquor) separated from the crystallized melamine according to this process cannot be directly recycled and reused to dissolve the melamine coming out of the reactor, because the concentration of OAT would increase continuously and, once the aqueous medium becomes saturated, OAT would precipitate together with the melamine crystals contaminating the product. For this reason, the mother liquor must be suitably treated before being recycled, in order to separate OAT and maintain their concentration in the mother liquor at a constant level below the solubility limit.

The aforesaid treatment not only renders the aqueous cycle of collection and purification of the melamine more complex, but also adds a source of costs, both in terms of investment and of energy consumption.

A schematic illustration of an embodiment of the process according to the above-mentioned U.S. Pat. No. 3,161,638 is shown in FIG. 1, representing the state of the art for the present invention, in order to demonstrate the advantages of the improvements to the aforesaid process brought about by the present invention.

According to the outline in FIG. 1, the urea is fed as a liquid at a temperature of 135–140° C. to a pyrolysis vat Reactor that works continuously and in which a suitable heating system supplies the necessary calories to the reacting system, maintaining it at a temperature of 360–420° C. The reaction pressure is maintained at a value above 7 MPa. The reactor is single-stage, and the reacting mass is maintained in strong circulation by the gases that are formed during the pyrolysis of the urea. The reacted mass (liquid and gas) is continuously discharged into an apparatus (Quench) where its temperature is lowered to approximately 160° C. in the presence of a water solution.

Under these conditions, all the melamine, the non-reacted urea and the various impurities, pass into solution and are sent downstream to be processed, while a gaseous phase, consisting substantially of $NH_3$ and $CO_2$, is separated and recycled to the urea synthesis plant, together with the amount of water vapor corresponding to the thermodynamic equilibrium in the Quench condition.

The aqueous solution from the Quench also contains a certain amount of dissolved ammonia and $CO_2$ that is eliminated in the following $CO_2$ Stripper. The elimination of the $CO_2$ is necessary in order to get a high degree of purity of melamine in the down-stream treatment.

The aqueous stream from the bottom of the $CO_2$ Stripper, containing a residual amount of $CO_2$ of 0.3–0.5% by weight, contains melamine at a concentration of 6–12% by weight, together with OAT and the polycondensates. The polycondensates, given their low solubility, must be eliminated before sending said aqueous stream to the Crystallizer for the recovery of the melamine.

In order to eliminate the polycondensates, the solution is heated to approximately 170° C. in the presence of ammonia in a suitable column, called Hydrolizer, in which ammonia is added to the warm solution until it reaches the level of 12–15% by weight. During the stay in the Hydrolizer under these conditions, the polycondensates are almost totally transformed into melamine and, to a lesser extent, into OAT.

The purified ammoniacal solution from the Hydrolizer is fed to the Crystallizer where the temperature is lowered to 40–50° C., thus allowing the crystallization of the greater part of the melamine. The presence of ammonia in the Crystallizer serves to maintain OAT in solution and thus to separate a product characterized by a high degree of purity (+99.9% weight). In the following operation of Liquid/Solid Separation, the crystallized melamine is separated from an aqueous stream containing the OAT formed in reaction and in the various pieces of equipment of the aqueous circuit due to the hydrolysis of melamine.

This aqueous stream (called mother liquor), in which the residual melamine is present at a concentration of 0.8–1% by weight, cannot be recycled directly to the Quench because, otherwise, the OAT content would continue to increase and, once the saturation concentration is reached, they would precipitate in the Crystallizer contaminating the product. On the other hand, the mother liquor cannot be discharged into the ambient because of the presence of large amounts of ammonia and other organic materials. Other than that, dumping the mother liquor would correspond to a heavy economic loss because of its melamine and ammonia content.

Therefore, the process according to U.S. Pat. No. 3,161,368 provides for the treatment of the mother liquor in De-Ammoniating Column. Here the ammonia is completely recovered and an ammonia-free solution is produced; this solution contains almost exclusively melamine and OAT. Cooling this solution to room temperature causes the Precipitation and Separation of OAT, which are thus eliminated from the aqueous cycle, allowing the re-circulation of the purified mother liquor and the recovery of the melamine contained in the mother liquor.

The process illustrated here above is currently in use industrially in numerous plants, but requires a certain consumption of steam, because almost the entire amount of the OAT-containing mother liquor must be heated. Furthermore, the presence of water in the stream of ammonia and carbon dioxide (off-gas) that are returned to the urea synthesis plant requires some adjustments in the operative conditions of the plant.

BRIEF SUMMARY OF THE INVENTION

The object of the present invention is a process for the production of melamine, which is greatly improved compared to the state of the art because: a) a substantially total recovery at low cost of the melamine dissolved in the mother liquor is enabled; b) a gaseous stream containing $CO_2$ and $NH_3$ completely free of water is separated and returned to the urea synthesis plant; c) a substantial increase in the total yield of the plant in terms of urea consumption is provided; d) the energy consumption of the entire process is considerably reduced; e) the number of processing steps is reduced, increasing the stream factor and the investment cost of the plant.

The object of the invention is achieved by a process that introduces simple but substantial modifications to the state of the art.

The main variations consist of the separation of off-gases from the product of pyrolysis of the urea before the treatment of melamine in the aqueous medium, and the introduction of a Post reactor, downstream of the pyrolysis Reactor, fed with the liquid phase containing all the melamine produced. The employment of a Post-reactor allows urea conversion to reach practically 100% and the amount of OAT produced in the reaction to be drastically reduced. The reduction of OAT allows, in the down stream, most of the mother liquor to be recycled directly to the Quenching Column without any treatment, permitting the direct recovery, without loss, of the corresponding amount of ammonia and melamine contained. Accordingly, the mother liquor, treated in the De-Ammoniating Column and in the OAT Precipitation and Separation Section, can be drastically reduced in comparison to the actual state of the art, with consequent reduction of investment and energy consumption.

BRIEF DESCRIPTION OF THE SEVERAL VIEWS OF THE DRAWINGS

The process of melamine synthesis according to the invention and the advantages that derive from it can best be understood from the following description of an embodiment of the present invention, with the aid of the attached FIG. 2. The description and the related outline of the process should not be considered as limiting the scope of the invention.

DETAILED DESCRIPTION OF THE INVENTION

Figure 1:
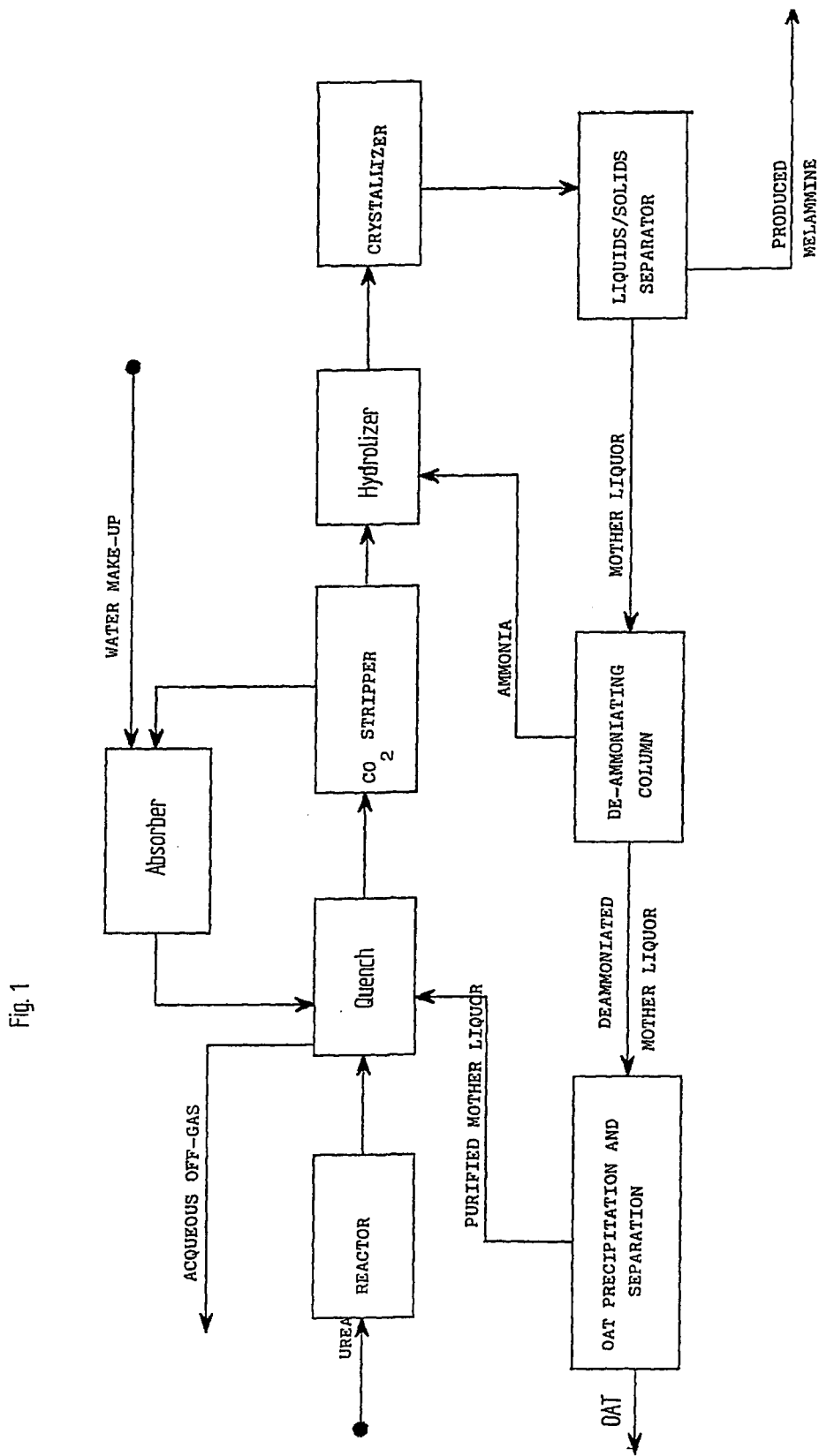
FIG. 1 is a schematic illustration of a process for the production of melamine according to the prior art.
Figure 2:
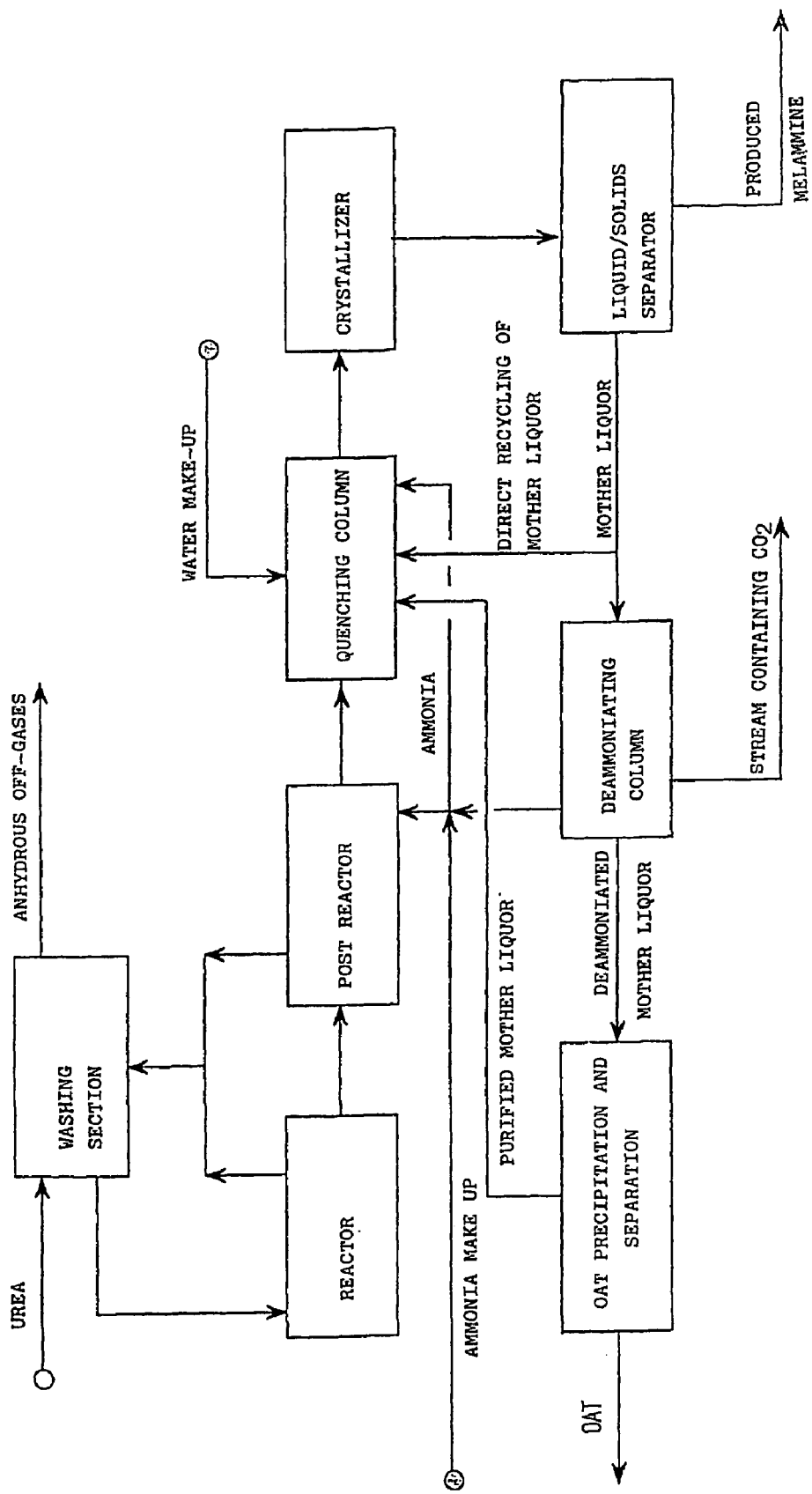
FIG. 2 is a schematic illustration of the main equipment and flow lines of the products and reagents of the process according to one embodiment of the invention.

The Reactor of FIG. 2 works in the same conditions as in FIG. 1, with the difference that there are two separate outputs from the Reactor: the off-gases output and the raw liquid melamine output. Neither of these outputs contains water.

The gaseous anhydrous stream of $NH_3$ and $CO_2$ containing vaporized melamine, in a proportion according to its vapor pressure, is fed to an off-gas Washing Section, operating at the same pressure as the pyrolysis reactor. In the off-gas Washing Section, the melamine is removed by direct contact with molten urea fed at a temperature of 135–140° C. By this operation, in which the considerable heat content of the off-gases is recovered as steam, the melamine is completely recovered by the molten urea and the resulting liquid mixture constitutes the input to the pyrolysis Reactor. The off-gases thus purified, leaving the Washing Section at a temperature of 170–200° C., are returned to the urea plant for the total recovery of $NH_3$ and $CO_2$. In a variant of this process, the gaseous fraction formed in the pyrolysis reaction can be separated in a suitable vessel placed downstream of the Reactor or in the same Post-reactor that, in such a case, also acts as a separator.

The molten urea containing the melamine recovered from the Washing Section feeds the Reactor by gravity or by means of a suitable pump.

The liquid stream of raw melamine leaving the Reactor is sent to the Post-reactor, which works under the same conditions of temperature and pressure as the Reactor, where it comes into intimate contact with superheated anhydrous gaseous ammonia added in amounts equal to from 1:10 to 1:1, typically 1:3 by weight of the raw liquid melamine.

The superheated ammonia passing through the liquid mass of the raw melamine extracts the dissolved $CO_2$ and enables the complete transformation of OAT into melamine.

The residence time of the melamine stream in the Post-reactor can vary from 0 to 2 hours, preferably from 15 to 45 minutes, obtaining a reduction of the OAT content to a value below 6,000 ppm.

This additional residence time of the liquid raw melamine stream in the Post-reactor also provides for the completion of the conversion of the urea. Moreover, with the elimination of the $CO_2$, the partial pressure of ammonia in the Post-reactor increases with consequent reduction of the polycondensates concentration.

The purified melamine exits from the Post-reactor containing reduced amounts of OAT and polycondensates and practically no residual urea.

The superheated ammonia blown into the Post-reactor remains substantially in the vapor phase and, exiting from the Post-reactor separately from the purified liquid melamine, joins the output gas from the Reactor before the off-gases Washing Section, where the recovery of the melamine present in the vapor phase occurs.

The purified liquid melamine stream is fed to the Quenching Column which, due to the absence of a gaseous phase, operates completely full of liquid. The purified liquid melamine enters at the bottom of the Quenching Column, which is kept strongly agitated by mechanical means, and is brought into intimate contact at a temperature of 160–170° C. with a water and ammonia solution coming from the purification circuit. The solution thus formed, in which the $NH_3$ content is maintained at a value above 10% by weight, proceeds upwards for sufficient contact time to transform the residual polycondensates coming from the Post-reactor into melamine. Since the concentration of $CO_2$ in the Quenching Column is very low (less than 0.1% by weight), effective hydrolysis of polycondensates is obtained in this column with very short contact times (under 30 minutes).

The aqueous solution of melamine from the head of the Quenching Column is fed directly to the Crystallizer where the temperature is lowered to 40–50° C., causing precipitation of crystals of very high-purity melamine, which are separated from the mother liquor in the next stage, the Liquid/Solid Separator.

The mother liquor in output from the Liquid/Solid Separator contains a reduced amount of OAT, far below the saturation value, since the OAT have been drastically reduced in the Post reactor. Therefore, the greatest part of the mother liquor can be recycled to the Quenching Column, without any treatment, with no risk of OAT reaching the saturation value in the Crystallizer with consequent precipitation.

According to the present embodiment, in order to stabilize the concentration of OAT in the circulating aqueous solution at a value prudentially far away from the value corresponding to the saturation in the Crystallizer condition, it is sufficient to send only a small part of the mother liquor to the De-Ammoniating Column and to the OAT Precipitation and Separation system. The portion of mother liquor undergoing treatment is in fact less than 20% of the output from the Liquid/Solid Separator. The less the amount of OAT output from the Post-reactor, the smaller this quantity will be. In other words, the higher the efficiency of the Post-reactor in reducing OAT, the smaller the portion of mother liquor which must be sent to the treatment and the greater the economic saving obtained in terms of investment cost and energy consumption.

The portion of mother liquor not directly recycled to the Quenching Column is subject to the same treatment as in the cycle illustrated in FIG. 1 and, after the separation and the recovery of the ammonia in the De-Ammoniating Column and the elimination of OAT in the OAT Precipitation and Separation section, that portion is also recycled to the Quenching Column, thereby enabling the total recovery of the melamine and ammonia. The concentration of $CO_2$, present in minimal amount in the purified output from the Post-reactor, is maintained constant in the circulating aqueous solution by continuously extracting a stream rich of $CO_2$ from a suitable point of the De-Ammoniating Column.

The present embodiment provides the following, considerable advantages:

1. The production of off-gases without water (anhydrous off-gases) and at a higher pressure facilitates their recovery in the urea plant to which they are returned. The economic value of anhydrous off-gases is higher than that of wet, lower pressure, off-gases produced by the process in the prior art.

2. The simplification of the aqueous purification circuit and the drastic reduction in the dimensions of the De-Ammoniating Column and the OAT Precipitation and Separation Section involve a net reduction of the investment cost, which exceeds the added investment for the Post-reactor vessel and the off-gas Washing Section. The system based on the process in the present embodiment provides for an investment reduction in excess of 15% compared with a plant in the prior art.

3. The total conversion of urea and the almost complete transformation of OAT into melamine in the Post-reactor involve an increase in overall yield of the process, corresponding to a reduction of at least 8% in consumption of the urea compared to the existing technology.

4. A further increase in overall yield of the process is due to the reduction of hydrolysis of the melamine into OAT in the aqueous cycle, because of the smaller numbers and volume of the pieces of equipment, in which the melamine remains in contact with aqueous solutions at a high temperature. The reduction of number and volume of the pieces of equipment in the aqueous cycle is consequent to the simplification of the same cycle and the drastic reduction in capacity of the De-Ammoniating Column.

5. The direct recycling of the greatest part of mother liquor from the Liquid/Solid Separator to the Quenching Column (with the consequent reduction of the fraction to be treated in the De-ammoniating column), provides for a reduction in energy consumption of more than 40% compared to the current process.

EXAMPLE

In a high-purity melamine production plant built in accordance with one embodiment of the invention and comprising all the stages included in the process of FIG. 2, 950 kg/hr of molten urea at a temperature of 135° C. are introduced into the Washing Section of the anhydrous off-gases coming from the reaction section.

The Washing operation is conducted at a pressure of 8 MPa and at a temperature of 185° C.

From the Washing Section are obtained 746 kg/h of anhydrous off-gases, free of melamine, that are sent to the adjacent urea synthesis plant, and a liquid mixture containing urea and the recovered melamine that is fed by gravity to the Reactor.

In the Reactor, the temperature is maintained at 380° C. and the pressure to 8 MPa for a residence time (calculated according to the entering molten urea stream) of approximately 50 minutes.

From the Reactor exit a raw melamine liquid stream containing 91% by weight of melamine and, separately, a gaseous mixture of $CO_2$ and $NH_3$ saturated with melamine vapors, which is sent to the off-gas Washing Section for the recovery of the melamine. The liquid stream is fed to the Post-reactor where, under the same conditions as in the Reactor, it is treated with a gaseous stream of 100 Kg/h of superheated anhydrous ammonia that almost totally eliminates the dissolved $CO_2$. The residence time of the liquid melamine in this piece of equipment is 45 minutes. The ammonia and gaseous $CO_2$ output from the Post-reactor joins the off-gases output from the Reactor and are fed together to the off-gas Washing equipment.

Molten melamine flows from the Post-reactor containing approximately 6000 ppm by weight of OAT and less than 1% by weight of polycondensates.

This purified melamine stream is fed to the Quenching Column, where it passes entirely into aqueous solution under conditions of 2.5 MPa and 170° C. The concentration of $NH_3$ in the Quenching Column is maintained above 13% by weight.

The aqueous solution output from the Quenching Column contains 7.8% by weight of melamine, less than 2500 ppm of OAT and less than 10 ppm of polycondensates. It is brought to almost atmospheric pressure and 45° C. in the Crystallizer. Under these conditions, 320 Kg/h of high-purity melamine (99.95% by weight) crystallizes and is separated in the Liquids/Solids Separator and dried. In the Liquid/Solid Separator, 4.85 $m^3$/h of mother liquor are recovered, of which 4 $m^3$/h return directly to the Quenching Column to dissolve the melamine coming from the Post-reactor, while the remaining 0.85 $m^3$/h are distilled in the De-Ammoniating Column where 70 kg/h of anhydrous ammonia and, as side-stream, 90 Kg/h of aqueous ammonia solution containing the $CO_2$ are recovered.

The de-ammoniated mother liquor from the De-Ammoniating Column, containing less than 700 ppm of $NH_3$, is cooled to 50° C. and the pH adjusted to the value of 7 by the addition of a small quantity of $CO_2$ in order to reduce the solubility of OAT to a minimum and cause its almost total precipitation. The precipitated OAT is separated by filtering and eliminated from the water cycle. The filtrate, consisting in a 1% melamine solution containing less than 200 ppm of OAT, is recycled to the Quenching Column, thus recovering the melamine contained in it.

While the invention has been described in connection with the above described embodiment, it is not intended to limit the scope of the invention to the particular forms set forth, but on the contrary, it is intended to cover such alternatives, modifications, and equivalents as may be included within the scope of the invention.

What is claimed is:

1. A process for the production of high-purity melamine comprising the steps of:
    (a) pyrolyzing urea in a reactor operating at a temperature comprised between 360 and 420° C. and at a pressure higher than 7 MPa, the reactor producing reaction products that comprise a gaseous phase and a liquid phase;
    (b) feeding the liquid phase from the reactor to a downstream post-reactor, the liquid phase from the reactor containing melamine, non-reacted urea, intermediate oxidized products of pyrolysis, dissolved carbon dioxide, and products of de-ammoniating condensation of melamine ("polycondensates"), the post-reactor operating at substantially equal conditions of temperature and pressure as the reactor and producing a liquid product, gaseous superheated anhydrous ammonia being fed under pressure to the post-reactor in order to eliminate the dissolved carbon dioxide and under conditions suitable for completing the pyrolysis reaction of the urea, for transforming the majority of the intermediate oxidized products of pyrolysis into melamine, and for decreasing the polycondensates concentration;
    (c) dissolving the liquid product from the post-reactor in an aqueous solution in a quenching column in the presence of ammonia and under conditions of temperature and residence time such to provide a solution substantially free of polycondensates, the solution substantially free of polycondensates being successively subjected to crystallization to provide purified melamine in solid phase and an aqueous mother liquor that contains melamine and reduced quantities of the intermediate oxidized products of pyrolysis, the mother liquor being recycled for the greater part directly to the quenching column without any further treatment; and
    (d) subjecting the anhydrous gaseous phase coming from the reactor and post-reactor to washing with molten urea, thereby recovering the melamine contained in the anhydrous gaseous phase as vapor, prior to returning the anhydrous gaseous phase to the urea synthesis plant for the recovery of the ammonia and carbon dioxide contained in it.

2. The process of claim 1, wherein the mother liquor not directly recycled to the quenching column is subject to treatment in a de-ammoniating column for the recovery of the ammonia and the elimination of the carbon dioxide dissolved in it, and wherein the mother liquor not directly recycled to the quenching column is successively sent to a precipitation and separation section for precipitating and separating the intermediate oxidized products of pyrolysis, the precipitation and separation section having the function of maintaining the concentration of the intermediate oxidized products of pyrolysis in the mother liquor constant at a level below saturation.

3. The process of claim 1, wherein the gaseous, anhydrous superheated ammonia is blown into the post-reactor in a ratio ranging from 1:10 to 1:1 with respect to the liquid phase from the reactor.

4. The process of claim 1, wherein the residence time in the post-reactor of the liquid phase from the reactor is comprised between 0 and 2 hours.

5. The process of claim 1, wherein melamine is recovered at reactor pressure and in anhydrous conditions by washing the gaseous phase containing melamine from the reactor and post-reactor with molten urea.

6. The process of claim 1, wherein the aqueous solution in the quenching column dissolving the liquid product from the post-reactor is maintained at a temperature of 160–170° C. in the presence of ammonia, the ammonia having a concentration above 10% by weight, the liquid product having a residence time of less than 30 minutes.

7. The process of claim 2, wherein the aqueous mother liquor subject to treatment in the de-ammoniating column and in the precipitation and separation section is in an amount comprised between 0 and 20% of the aqueous mother liquor recovered after crystallization.

* * * * *